United States Patent [19]

Ebersole et al.

[11] Patent Number: 5,135,852
[45] Date of Patent: Aug. 4, 1992

[54] PIEZOELECTRIC CELL GROWTH BIOSENSING METHOD USING POLYMER-METABOLIC PRODUCT COMPLEX INTERACTIONS

[75] Inventors: Richard C. Ebersole, Wilmington; Robert P. Foss, Hockessin; Michael D. Ward, Newark, all of Del.

[73] Assignee: E. I. Du Pont de Nemours and Company, Wilmington, Del.

[21] Appl. No.: 384,813

[22] Filed: Jul. 25, 1989

[51] Int. Cl.$^5$ .................. C12Q 1/04; C12Q 1/06; G01N 33/566
[52] U.S. Cl. ..................... 435/39; 435/34; 436/501; 436/806; 436/908
[58] Field of Search ............... 435/817, 29, 34, 39; 422/82.01, 88, 98, 68.1; 436/806, 908, 502; 73/61 R, 24.03, DIG. 4

[56] References Cited

U.S. PATENT DOCUMENTS

| | | |
|---|---|---|
| 4,236,893 | 12/1980 | Rice . |
| 4,242,096 | 12/1980 | Oliveira et al. ............ 436/806 |
| 4,314,821 | 2/1982 | Rice . |
| 4,390,620 | 6/1983 | Junter et al. ............ 435/817 |
| 4,735,906 | 4/1988 | Bastiaans . |
| 4,847,193 | 7/1989 | Richards et al. ........... 436/806 |
| 4,999,284 | 3/1991 | Ward et al. .............. 435/4 |

FOREIGN PATENT DOCUMENTS

| | | |
|---|---|---|
| 215669 | 3/1987 | European Pat. Off. . |
| 239613 | 4/1987 | European Pat. Off. . |
| 276142 | 7/1988 | European Pat. Off. . |
| 295965 | 12/1988 | European Pat. Off. . |

OTHER PUBLICATIONS

O. Fatibello-Filho et al., Piezoelectric Crystal Monitor for Carbon Dioxide in Fermentation Processes, Anal. Chem. (1989) 61, 746–748 No. 7, Apr.
Dialog Information Service, File 351, World Patent Index 1981–1990, Accession No. 2987968, JP-A-57050652.
Guilbault, et al, CRC Crit. Rev. in Anal. Chem., vol. 19, Issue 1, "Analytical Uses of Piezoelectric Crystals: A Review" (1988).
Fawcett, et al, Analytical Letters, vol. 21, Issue 7, pp. 1099–1114, (1988).
Shons, et al, Jrl. Biomed. Mater. Res., vol. 6, pp. 565–570 (1972).
Ngeh-Ngwainbi, et al, J. Am. Chem. Soc., vol. 108, pp. 5444–5447 (1986).
Grabbe, et al, J. Electroanal. Chem., vol. 223, pp. 67–78, (1987).
Roderer, et al, Anal. Chem., vol. 55, pp. 2333–2336, (1983).

Primary Examiner—David L. Lacey
Assistant Examiner—Jan M. Ludlow

[57] ABSTRACT

The invention relates to a piezoelectric biosensor device and also to a method and a system utilizing a piezoelectric biosensor device for detecting metabolic growth requirements, antibiotic responses, and the specific bacterial products of microorganisms. When a microorganism is grown in an appropriate nutrient medium containing a metabolic product responsive polymer, metabolic products of the organism acidify the medium and precipitate a polymer metabolic product complex which deposits or accumulates on the surface of a piezoelectric biosensor device. The mass change on the surface of the device resulting from this deposit produces a change in the resonant frequency of the piezoelectric biosensor device which can be used to determine the growth and type of microorganism.

15 Claims, 12 Drawing Sheets

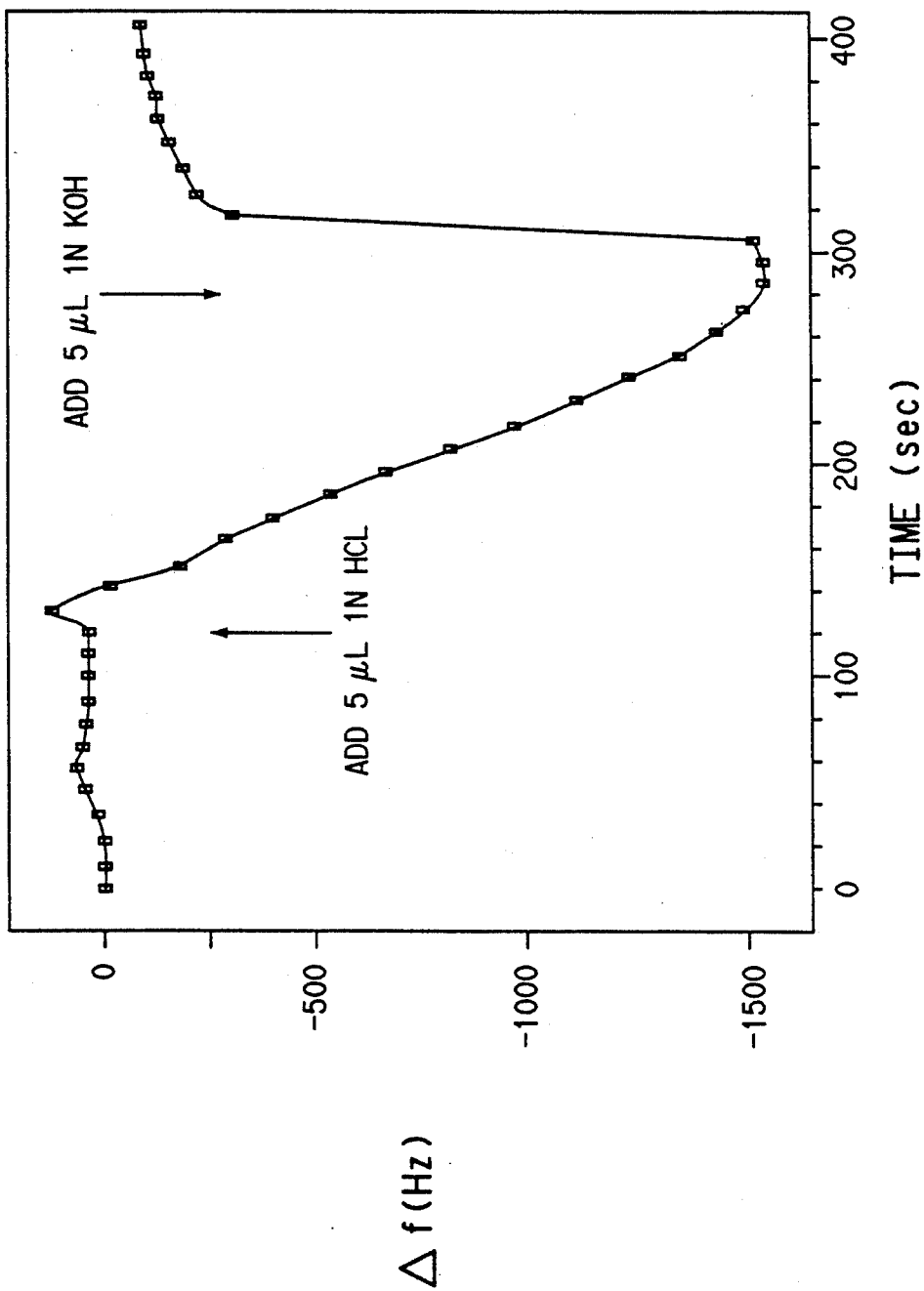

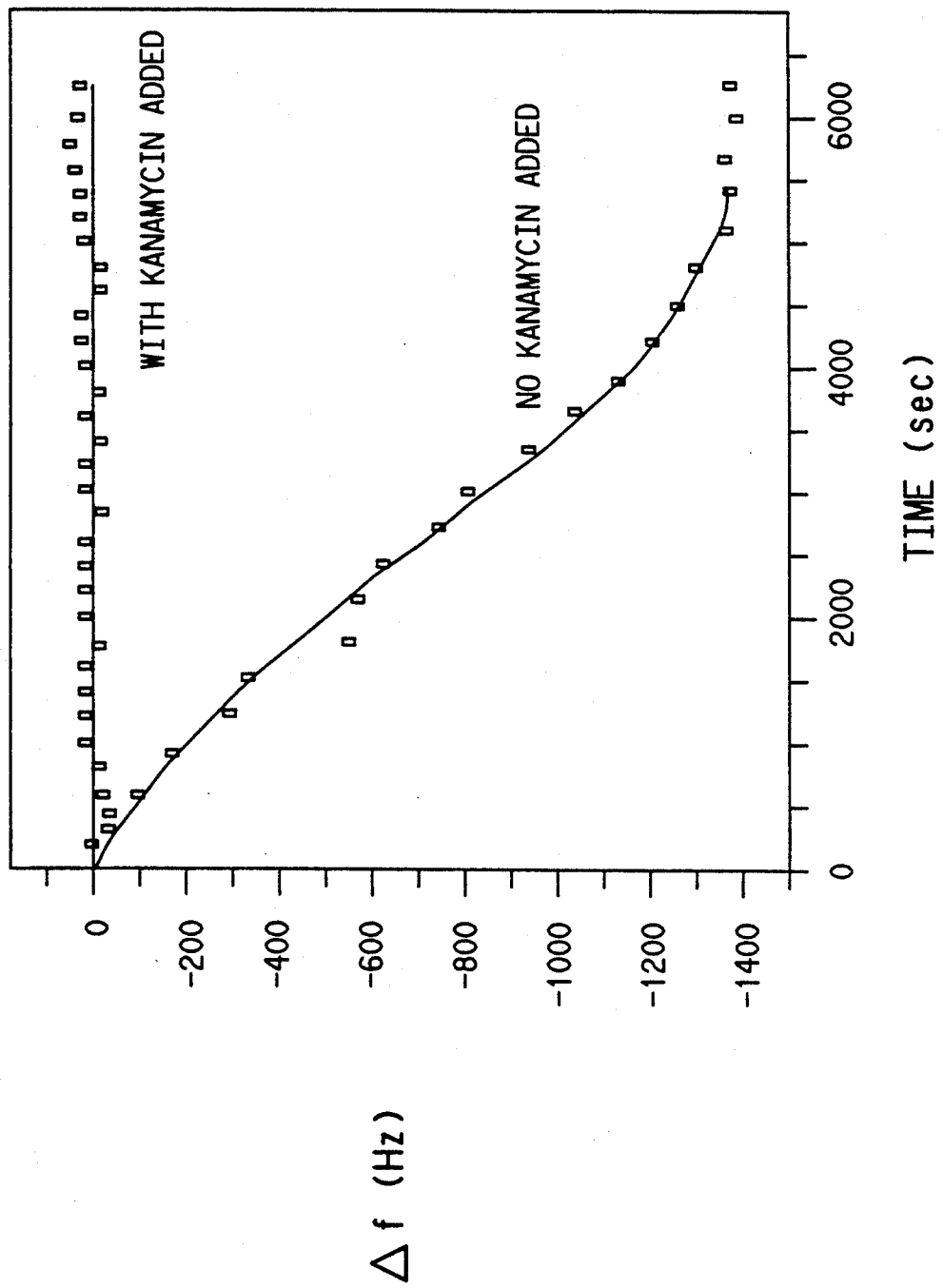

PIEZOELECTRIC CELL GROWTH BIOSENSING METHOD USING POLYMER-METABOLIC PRODUCT COMPLEX INTERACTIONS

TECHNICAL FIELD

The invention relates to a piezoelectric biosensor device for detecting the presence of organisms and also to a method and a system utilizing a piezoelectric biosensor device for detecting growth, metabolic requirements, antibiotic responses, and the specific products of microorganisms, and for determining organism doubling rates. When an organism is grown in an appropriate nutrient medium metabolic products of the organism react with metabolite product responsive polymer. This reaction induces deposition or accumulation of the altered polymer on the surface of a piezoelectric biosensor device. The mass change on the surface of the device results in a change in the resonant frequency of the piezoelectric biosensor device. This invention provides a versatile method for determining the growth rate, antibiotic sensitivity and cell type of organisms grown in culture by means of a piezoelectric oscillator.

BACKGROUND OF THE INVENTION

Conventional analytical measures to characterize cell growth and type suffer from substantial weaknesses. By itself, cell morphology is an unreliable means of cell identification. Morphological features can not be observed consistently, are inadequate for definitive identification, or require painstaking microscopic examination. Immunoassays and DNA probe assays can provide sensitive and specific characterizations of cells. However, these techniques have multiple drawbacks. They require the use of reagents which are complex and difficult to prepare. The assays themselves are complicated and time-intensive to perform. Often, the narrow specificity of an assay precludes development of a test that will respond to all strains of a single cell species.

This invention seeks to overcome these deficiencies by exploiting the metabolic functions of organisms and to offer a tool for characterization of organism growth and type with significant advantages over alternative analytical measures.

During the growth of microorganisms and cells, the composition of the supporting growth medium is altered as nutrients are converted by the organisms into metabolic end products. For example, complex molecules such as carbohydrates and lipids are converted by the cell's metabolic processes into smaller molecules such as lactic acid, succinic acid, acetic acid, or bicarbonate. Polypeptides and proteins are converted by way of amino acids to ammonia and bicarbonate. Thus, as growth occurs, the hydrogen ion content of the media changes as the starting nutrients are converted into metabolic products.

While these effects have been widely exploited by microbiologists for detection and identification of microorganisms using various manual and automated testing devices, piezoelectric oscillators have not been used previously in conjunction with metabolic products of cells to improve detection and analysis capabilities.

Previous efforts to apply piezoelectric oscillator techniques to biological activity require a time-consuming preparatory step in which one or more receptor materials, often antigens or antibodies, are immobilized on the surface of the piezoelectric oscillator. During operation of the piezoelectric oscillator, the receptor material binds with the target cell or analyte in a highly selective manner. The analyte drawn from solution may be complementary antibodies, antigens, DNA, or whole cells. Addition of the analyte changes the crystal's resonant frequency ($\Delta f$), the magnitude of which is proportional to the solution analyte concentration. This approach is described in UK Patent Application No. 86307115.5 by Seiko.

However, preparation of these receptor-modified piezoelectric devices is procedurally complex and often difficult. Even careful preparation does not guarantee consistent results. Receptor reagents are expensive, can inactivate during the immobilization process, and can separate from the surface of the crystal after immobilization. (G. G. Giulbault, J. H. Luong, and E. Pursak-Sochaczewski, Biotechnology, vol. 7, pp. 349-351, 1989.). Known techniques also require either washing or drying of the QCM (quartz crystal microbalance) or separation of "free" or "bound" reagents before QCM measurement. As a result, receptor-modified piezoelectric methods are not suited to continuous real-time measurement of metabolite production. Finally, the usefulness of receptor-modified piezoelectric methods is limited by the specificity of the reagents. It is extremely difficult to find a single reagent that responds broadly to many different cell strains or types, and thus repeated testing to assess the presence of different cell types has been necessary.

There currently exists a clear need for a piezoelectric method to detect, measure and analyze the growth of organisms in a way that overcomes the deficiencies of the existing technology. The ideal method should provide means of continuous detection, be simple to operate, economical, and quick, and should be useful for testing in a variety of different growth media compositions. The method should not require an immobilized receptor or complex washing and separation steps. The method should enable simultaneous tests using uncomplicated reagents. Unlike immunoassays or DNA probe assays, the method should be broadly applicable to all strains derived from a given species. The method also should be capable of detecting particular cells and microbes in the presence of mixed flora without prior separation into pure cultures. Thus, real time monitoring of the mixed culture would be available. Additionally, the method should be computer compatible so as to conveniently provide for statistical analysis of accumulated data. A device and a system to achieve these ends is also needed.

SUMMARY OF THE INVENTION

A method, a device, and a system for detecting a wide variety of organisms by means of a piezoelectric oscillator have been discovered. The piezoelectric oscillator accumulates a complex of a specific metabolic product responsive polymer and the specific metabolic product produced by the organism once the metabolism of the organism has changed the conditions of the culture medium. Specifically, one aspect of this invention is a method for detecting the presence of a particular organism or its growth over time comprising the steps of (1) measuring the resonant frequency of the piezoelectric oscillator by contacting a piezoelectric oscillator with a medium containing a specific metabolic product responsive polymer and a growth regulator; (2) introducing into the medium an organism capable of producing a metabolic product; (3) incubating the medium; (4) reacting the metabolic product with the metabolic product responsive polymer to yield a polymer-metabolic product complex; and (5) monitoring the medium for a change in the resonant frequency of the piezoelectric oscillator caused by the accumulation of the metabolic product responsive polymer on the piezoelectric oscillator when the isolectric point of the polymer complex is reached. Another aspect of this invention includes a device for detecting organisms comprising (1) a piezoelectric oscillator on which is deposited a complex of metabolic product and metabolic product responsive polymer as described above; (2) a source of power connected to the piezoelectric oscillator; and (3) a means connected to the piezolectric oscillator to measure its change in resonant frequency. A further aspect of this invention includes a system for detecting an organism comprising (1) a piezoelectric oscillator on which is deposited a complex of a metabolic product and a metabolic product responsive polymer; (2) a reagent delivery system; (3) a source of power connected to the piezoelectric oscillator; (4) a means connected to the piezoelectric oscillator to measure its change in resonant frequency; and (5) a computer to collect, store and analyze the data generated by the system.

BRIEF DESCRIPTION OF THE DRAWINGS

The invention can be more fully understood from the following detailed description thereof in connection with accompanying drawings which form a part of this application and in which:

FIG. 6b is a graph showing changes in the resonant frequency of a QCM during electrochemical manipulation towards the isoelectric point of the metabolic product responsive polymer contained in a solution.

FIG. 7 is a graph comparing the resonant frequency response over time for E. coli culture with and without Kanamycin.

DETAILED DESCRIPTION OF THE INVENTION

Figure 1:
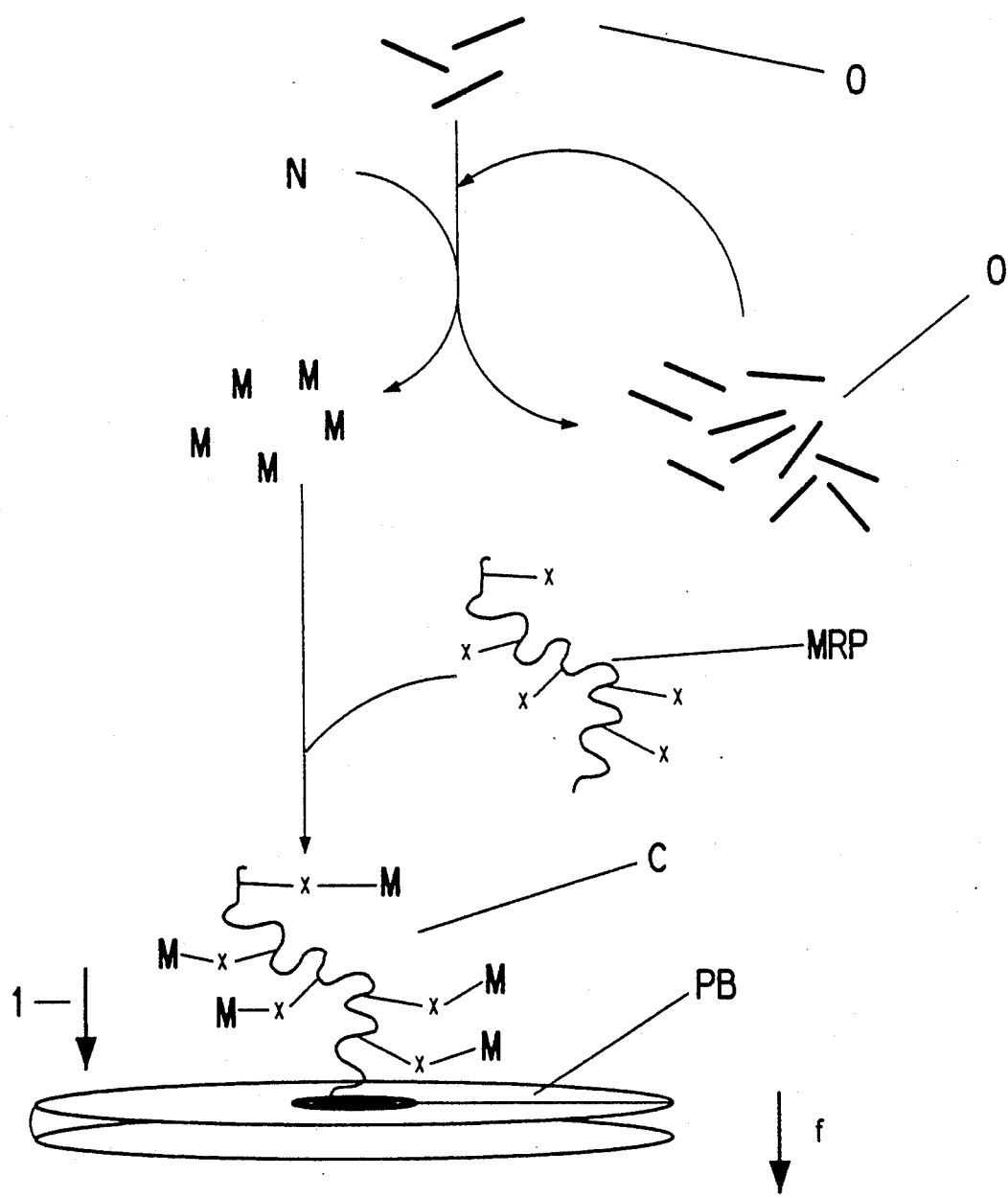
FIG. 1 is a diagram showing the general principle of the invention using a metabolic product responsive polymer.

Applicant's invention relates to a piezoelectric biosensor device, a system and a method for detecting the presence of living organisms by exploiting the interactions of a metabolic product responsive polymer with the metabolic products produced by the living organisms. These interactions induce deposition or accumulation of the polymer/metabolic product complex on the surface of a piezoelectric biosensor device. The mass change on th surface of the device results in a change in the resonant frequency of the piezoelectric biosensor device. This invention provides a versatile method, a device, and a system by which metabolism-related changes in an organism's culture medium can be monitored using piezoelectric detection principles.

In the context of this disclosure, a number of terms will be used. As used herein, metabolic product is referred to any substance which has been metabolically altered or produced by the cell. The substance can be degraded into two smaller products or used in synthesis of new compounds. The metabolic product may be found free in surrounding media, attached to the cell surface or contained within the cell. "Metabolic product responsive polymers" are those polymers which 1) interact with a metabolic product, 2) amplify the mass of the metabolic product, 3) interact with the piezoelectric oscillator after reaction with a metabolic product to alter its frequency, 4) are water-soluble, and 5) are physiologically compatible. "Amphoteric polymers" are those metabolic product responding polymers which have the capacity to behave as either an acid or a base. Amino acids and proteins are amphoteric since they contain both an acid group (COOH) and a basic group ($NH_2$). "Amphoteric metabolic product responsive polymers" refer to polymers which possess the characteristics of metabolic product responsive polymers and amphoteric polymers. "Piezoelectric oscillator," "quartz crystal microbalance," and "QCM" are three terms referring to a biosensing device using piezoelectric principles as the basis for detecting changes in mass. In addition, SAW (surface acoustic wave), bulkwave oscillators, and flexural plate-mode devices are alternative devices for use in detecting mass changes. As used herein, "organism" includes any organism which, as a result of its metabolism, makes a product unique to that organism that can be detected or identified by the method of this invention. The organisms for which this invention will be most useful, however, are microorganisms normally grown in aqueous cultures, such as bacteria, fungi, and tissue cells. "Growth regulators" are those substances that stimulate or retard the growth of the organism. "Nutrients" are those substances metabolized by the organism and necessary for growth. "Receptors" are compounds that form specific binding pairs with an analyte. These may take the form of chelating agents, antibodies, lectins, tissue receptors, cellular adhesion factors, and ligand binding proteins.

Unlike the earlier techniques described above, the preferred embodiment of the instant invention does not rely on prior modification of the crystal surface with receptors. Instead, a piezoelectric oscillator with an unmodified crystal surface is used. Alternative means to meet the invention's objectives are also described.

FIG. 1 illustrates the general principles and elements of the invention for the detection and analysis of microorganisms. Organisms (O) metabolize nutrients into metabolic products (M) such as acids, buffering ions, salts, enzymes, proteins, carbohydrates, and lipids. The growth medium selected to culture the organisms contains, in addition to nutrients (N), a metabolic products responsive polymer (MRP) specially designed 1 to be non-reactive with the piezoelectric biosensor (PB) and to be reactive with a specific metabolic product (M). The introduction of this metabolic product (M) into the nutrient medium alters the metabolic product responsive polymer (MRP) and forms a polymer/metabolic product complex (C). The complex interacts with the gold electrode of the piezoelectric biosensor (PB) and changes the device's resonant frequency ($\downarrow$ f). This interaction is shown by the arrow (1). The polymer/metabolic product complex (C) accumulates on the oscillator as the pH of the medium approaches the isoelectric point of the complex. The degree of resonant frequency shift is proportional to the amount of metabolic product produced by the organism and present in the medium. In this way, the change in resonant frequency is related to the metabolism and rate of growth of the organism.

Figure 2:
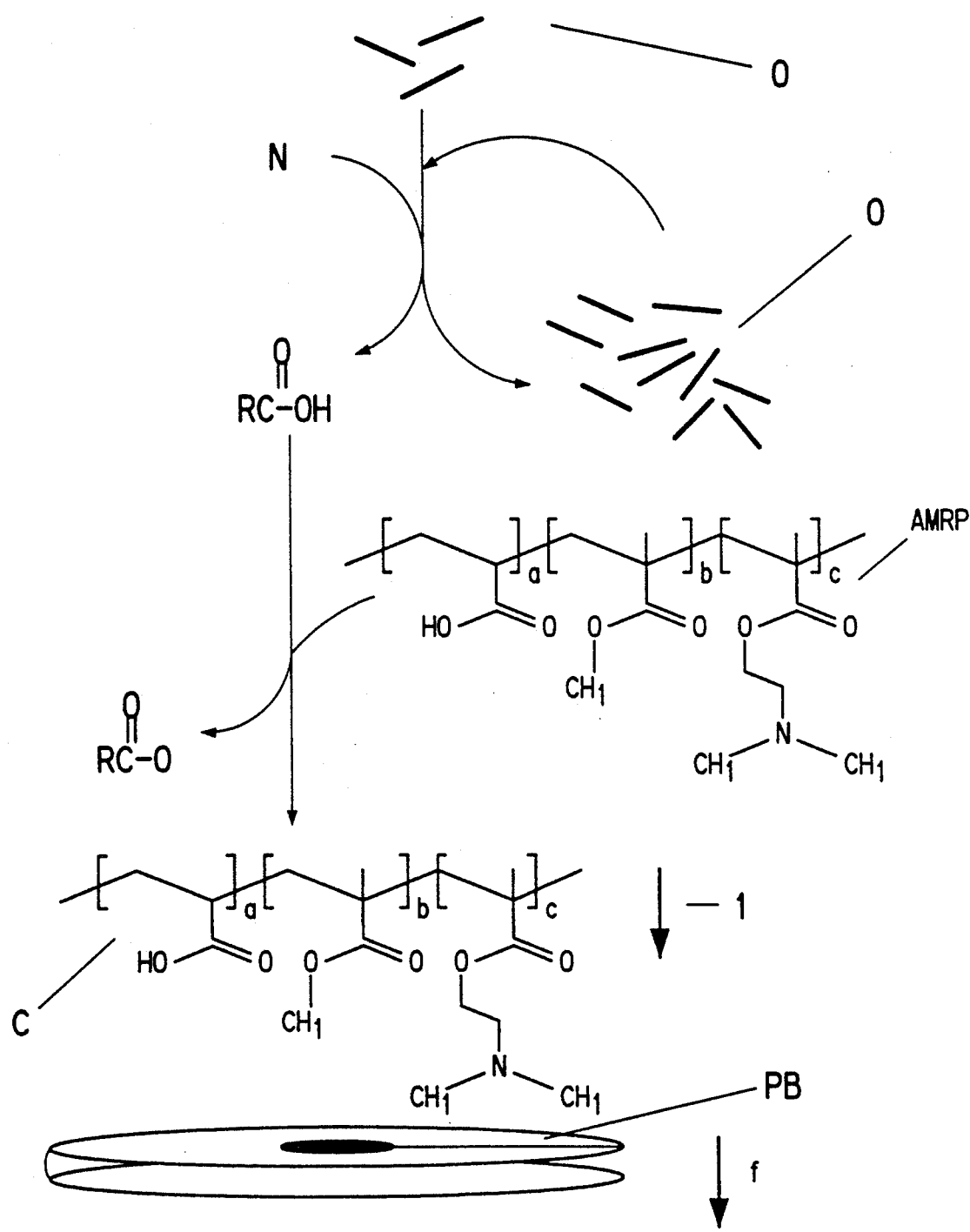
FIG. 2 is a diagram of the invention showing the interaction of H+ with the metabolic product responsive polymer.

The polymer is chosen or designed to react with a metabolic product through ion pairing, complexation reactions, redox reactions, or covalent coupling. This variety of reactions enables the invention to apply equally well to large or small molecular weight metabolic products. For convenience, "complex" as used herein refers to the substance resulting from the reaction of a metabolic product responsive polymer with a metabolic product regardless of the the specific mechanism involved. FIG. 2 is structurally similar to FIG. 1 and more specifically illustrates the use of a polymer designed to react with acidic metabolic products. When metabolic organic acids or carbon dioxide acidify the growth medium, protons released by the metabolic products react with proton receptor groups on the amphoteric metabolic product responsive polymer (AMRP). Proton neutralization changes the net charge on the polymer and which alters the physical properties of the polymer. The isoelectric polymer/metabolic product complex (C) accumulates on the oscillator as the pH of the medium approaches the isoelectric point of the complex. The complex interacts with the gold electrode of the piezoelectric biosensor (PB) and changes the device's resonant frequency ($\downarrow$ f). This interaction is shown by the arrow (1). The deposit on the piezoelectric oscillator gives a corresponding frequency decrease that can be read electronically to determine the metabolism rate and cell growth rate of a culture.

Figure 3:
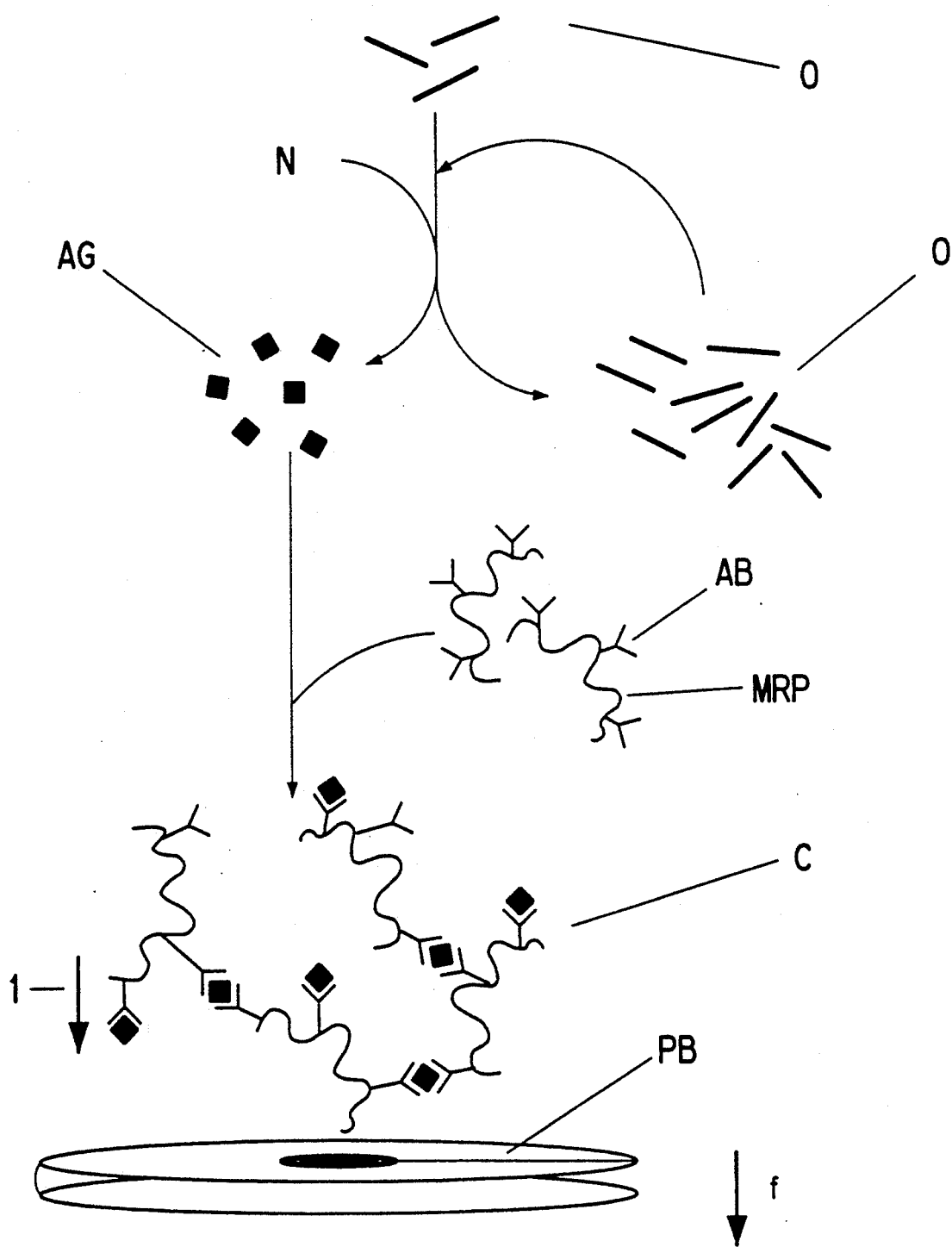
FIG. 3 is a diagram of the invention showing a metabolic product responsive polymer possessing metabolic product specific binding sites.

The selectivity of the polymer/metabolic product interaction also can be controlled by the design of the polymer. For example, antibodies, polynucleic acids, receptors, chelating agents, cellular adhesion factors, and ligand binding molecules can be linked to the polymer. By varying the number of these receptor sites on the polymer, the invention can be made highly selective for a specific metabolic product or broadly responsive to a number of metabolic products. FIG. 3 is similar in structure to FIG. 1 and more specifically illustrates this application of the invention. A good example is an antigen (AG) produced by the organism (O) which complexes with a polymer (MRP) constructed to contain the complementary antibody (AB) as a receptor. Changes in solubility and physical properties of the resulting antigen/antibody-polymer complex (C) induce its association with the surface of the piezoelectric biosensor (PB). The complex interacts with the gold electrode of the piezoelectric biosensor (PB) and changes the device's resonant frequency ($\downarrow$ f). This interaction is shown by the arrow (1). As in other cited examples, monitoring of the resonant frequency of the piezoelectric oscillator provides a specific measurement of the amount of metabolic product or the rate of metabolic product production in the medium.

PIEZOELECTRIC OSCILLATOR

Piezoelectric oscillators to record changes in mass are well described in the literature. One type of oscillator consists of a single crystal wafer sandwiched between two electrodes (QCM). The electrodes are provided with means for connection to an external oscillator circuit that drives the quartz crystal at its resonant frequency. This frequency is dependent on the mass of the crystal, as well as on the mass of any layers confined to the electrode areas of the crystal. Thus, the frequency is altered by changes in mass on the surface of the electrodes or in any layers on those electrodes. In general, the change in resonant frequency of these devices can be correlated to the amount of mass change. If the QCM and any attached layers obey rigid-layer behavior, the mass changes are determined from the shift in the resonant frequency according to the Sauerbrey relationship $$\Delta f = - \frac{2 f_0^2 \Delta m}{A \sqrt{\rho_q \mu_q}}$$

where $\Delta f$ is the measured frequency shift, $f_0$ is the parent frequency of the quartz crystal, $\Delta m$ is the mass change, $A$ is the piezoelectrically active area, $\rho_q$ is the density of quartz (2.648 g cm$^{-3}$) and $\mu_q$ is the shear modulus (2.947 $\times$ 10$^{11}$ dynes cm$^{-2}$ for AT-cut quartz).

The resonant frequency of the piezoelectric oscillator is also affected by changes in the viscosity of the medium. The frequency shift upon a viscosity change can be determined by the following relationship $$\Delta f = f_0^{3/2} (\eta \rho / \pi \mu_q \rho_q)^{\frac{1}{2}}$$

where $\eta$ is the viscosity of the medium and $\pi$ is the density of the medium.

Surface acoustic wave (SAW) devices represent an alternative piezoelectric transduction technique applicable to this invention. These devices comprise interdigitated microelectrode arrays on the surface of a piezoelectric quartz substrate. They exhibit frequency changes that can be correlated with mass changes at their surface arising from changes in the velocity of a transverse surface wave. SAW devices have also been employed as viscosity sensors. Flexural plate-mode devices represent another alternative technology capable of measuring mass changes at the surface of a piezoelectric substrate. These latter two devices differ from the QCM in that they are responsive not only to mass changes, but also to changes in the stiffness coefficient of the bound layers.

METABOLIC PRODUCT-RESPONSIVE POLYMERS

The specific polymers used as metabolic product-responsive polymers for the examples of the instant piezoelectric biosensing device are amphoteric co- or ter-polymers of acrylic acid (AA), alkyl methacrylate (RMA), and N,N-dimethylaminoethyl methacrylate (DMAEMA). Structurally, the polymers may be linear or may contain pendent or cross linking chains. They are prepared using a two-step process. The first step produces a prepolymer from methyl acrylate (MA), RMA and DMAEMA. The second step involves the controlled selective hydrolysis of methyl acrylate segments to form a product with pendant acid and base groups. The reactions are represented as follows:

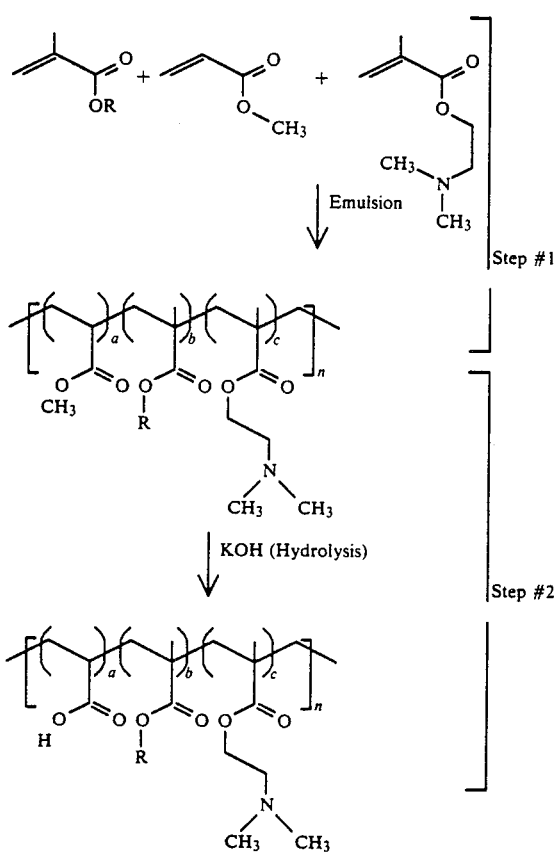

A two-step emulsion process is preferred over direct solution polymerization for the following reasons. Michael addition of the amine to acrylic acid monomer is more easily prevented. Emulsion polymerization of prepolymer is significantly faster and more easily controlled than solution polymerization. In addition, the composition distribution of monomer units in the polymer is far more easily regulated by controlled feed methods.

The polymers are generally soluble in water at all pH's other than their isoelectric points (pI). The isoelectric point is determined by the ratio of acid to base groups and thus can be varied by synthesizing polymers with appropriate ratios. The preferred ratio for polymers used in the instant invention is such that the polymer's pI is in the physiological region (~6.2-7.8). This normally corresponds to a ratio of acid to base of 2.0 to 0.8 for acrylic acid and DMAEMA. (The pI is necessarily dependent on the pKa values for the component groups.) Responses can also be affected by the nature and size of the neutral, non-ionic segment, which can influence the pK of the component acid and base moieties.

The solubility characteristics of the polymers are strongly influenced by their ion content. Polymers having significant neutral hydrocarbon segments are less water-soluble at their isoelectric point than polymers with little or no neutral segments. Applicants have prepared a series of polymers containing different alkyl methacrylates and having variable segment fractions, all with pI's in the physiological range. Several other polymers having different solubility and associative characteristics are also predicted to be suitable. Some of these polymers are listed in Table A.

TABLE A
POLYAMPHOLYTES FOR PIEZOELECTRIC DETECTION OF BACTERIA GROWTH

| Composition M.V. | Molar Ratio* Est.* | Calc. from C,H,N | pI | M. Wt. |
|---|---|---|---|---|
| AA-MMA-DMAEMA — | 1-1-1 | — | 6.53 | — |
| AA-MMA-DMAEMA 12200 | 1-1-1 | 1.05/1.36/1 | 7.63 | 14800 |
| AA-MMA-DMAEMA 35800 | 1-1-1 | 1.014/1.12/1 | 6.95 | 45300 |
| AA-MMA-DMAEMA 30200 | 1-1-1 | 1.03/1.21/1 | 7.39 | 38700 |
| AA-MMA-DMAEMA 30300 | 1-2-1 | 1.06/2.46/1 | 7.11 | 39400 |
| AA-EMA-DMAEMA 70700 | 1-1-1 | — | 7.30 | 100000 |
| AA-BMA-DMAEMA 224000 | 1-1-1 | 1.083/1/1 | 7.50 | 350000 |
| AA-MMA-DMAEMA 68400 | 1-3-1 | 1.035/3.38/1 | 7.46 | 99000 |
| AA-MMA-DMAEMA 36000 | 4-5-1 | 4.69/6.36/1 | 5.37 | 45600 |
| AA-MMA-DMAEMA 67800 | 2-3-1 | 2.08/3.25/1 | 6.57 | 97200 |
| AA-MMA-DMAEMA 136000 | 1-3-2 | 1/3.22/2 | 8.14 | 204000 |

Figure 4:
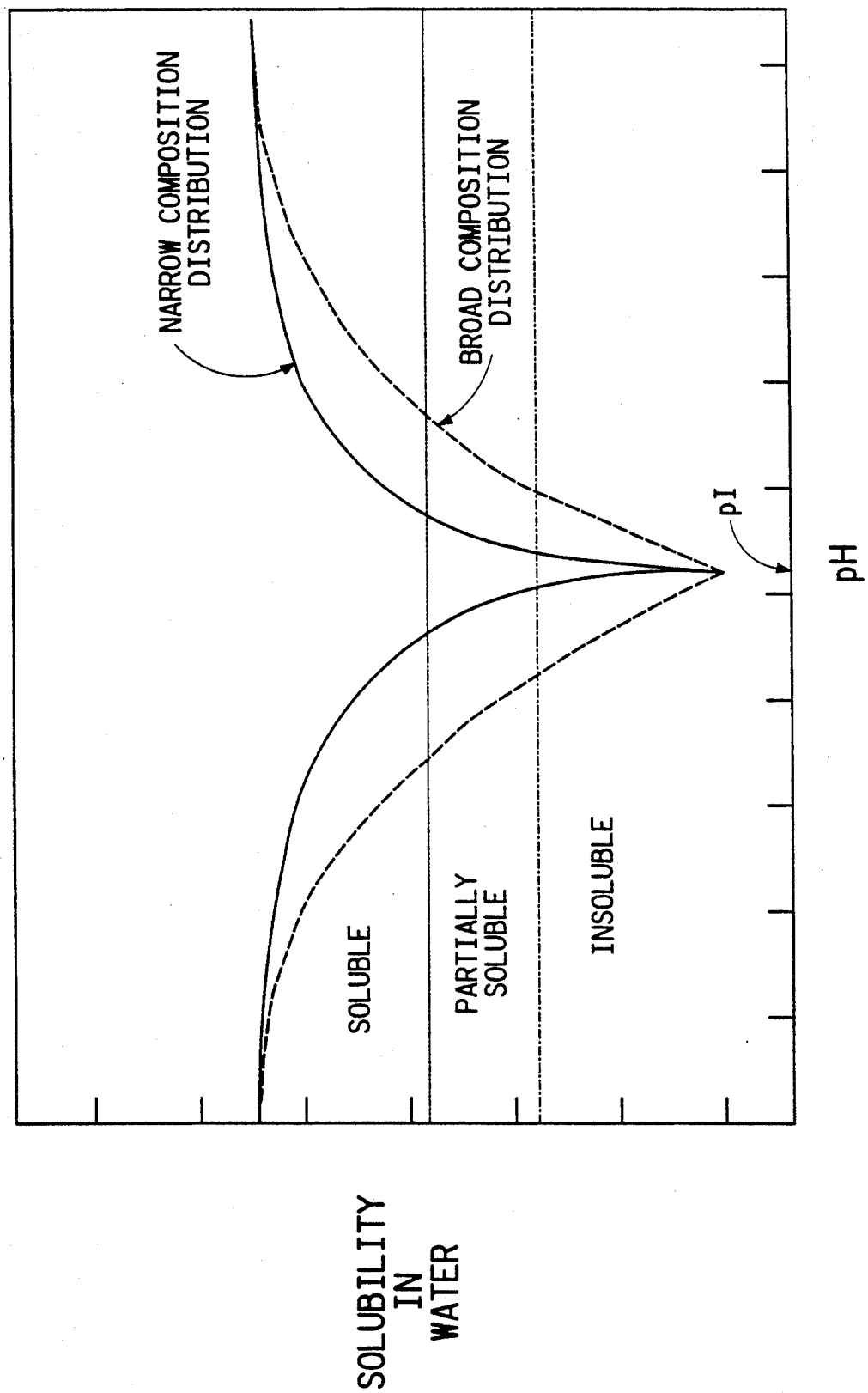
FIG. 4 is a graph showing the effect of reaching the pI of materials with narrow and broad composition distributions.

AA = acrylic acid
RMA = alkyl methacrylate
DMAEMA = N,N-dimethylaminoethyl methacrylate
MA = methyl acrylate
EMA = ethyl methacrylate
BMA = butyl methacrylate
MMA = methyl methacrylate
Mw = Weight-average molecular weight
Mv = Viscosity-average molecular weight
*Approximate mole ratios listed The sensitivity of the polymer to small changes in pH is largely dependent on the narrowness of its composition distribution. This is represented in FIG. 4. A narrow composition distribution is generated by controlling the ratio of reacting monomer in the reaction medium. This ratio is not that found in the polymer but is determined by the reactivity ratios of the constituent monomers. The ratio can be maintained by using either a balanced feed or a starved feed reaction process. The balanced feed process described in U.S. Pat. Nos. 4,735,887 and 4,749,762 requires careful reaction control, but leads to rapid formation of high molecular weight product. The starved feed process is preferable when rapid production of high molecular weight product is unnecessary. The starved feed process involves the addition of feed monomer at a rate much lower than its bulk reaction rate in neat media. The reaction becomes essentially a living free radical process, occurring only when monomer encounters an emulsion particle containing a living radical. Enough "balance monomer" is added to saturate the aqueous phase (determined as the point where the solution starts to develop translucence), before starting addition of initiator. A slight excess of MA should also be maintained to give the correct product composition. This is easily accomplished because of the favorable relationship between total inherent reaction rate and reactivity ratios for the acrylate-methacrylate system.

Many combinations of monomer are capable of yielding polymers having pI's in the physiological pH range. Amphoteric polymers can be prepared from various combinations of the following sets of monomers set out below:

A. Acidic monomers—Molecular or ionic substance that can yield a hydrogen ion to form a new substance. Examples are acrylic acid, methacrylic acid, and monomers containing phosphoric acid and sulfinic acid groups.

B. Basic monomers—Molecular or ionic substance that can combine with a hydrogen ion to form a new compound. Examples are DMAEMA, diethylaninoethyl methacrylate, t-butylaminoethyl methacrylate, morpholinoethyl methacrylate, piperidinoethyl methacrylate.

C. Neutral monomers—Molecular or ionic substance that is neither acidic or basic. Examples are alkyl methacrylates (MMA, EMA, BMA), hydroxyethyl methacrylate (HEMA), hydroxypropyl methacrylate, vinyl pyrrolidone, vinyl acetate (vinyl alcohol on hydrolysis), acrylamides, vinyl ethers, styrene. (Reaction of co-monomers having vastly differing reactivity ratios requires very careful reaction control and therefore is not preferred.)

In addition to the examples set out above and in Table A, any aqueous soluble amphoteric polymer with an pI in the physiological range may be useful as a pH sensitive metabolic product responsive polymer. Specific examples include:

1) Polymers generated by the reaction of dimethylamino ethanol and similar compounds with methylvinylether/maleic anhydride co-polymers.

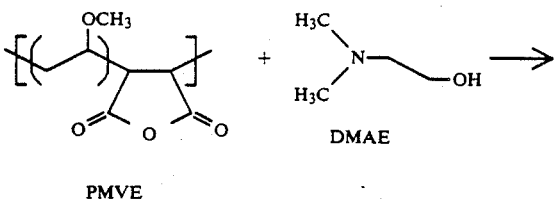

PMVE

DMAE

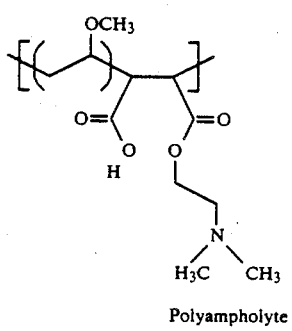

Polyampholyte

2Hydrolyzed co-polymers of vinyl pyridine and methyl acrylate.

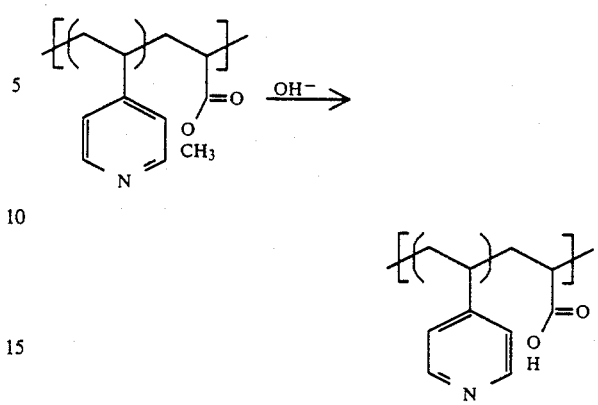

Still other metabolic product responsive polymers can be formed by linking antibodies, polynucleic acids, receptors, chelating agents, cellular adhesion factors, and ligand binders to aqueous soluble polymers containing pendent hydroxyl, carboxyl, amino, thiol, aldehyde, anhydride, imide and epoxy groups. In the process, the polymer containing one or more of these pendant groups is reacted with a linking agent to form an intermediate group that is reactive toward the metabolic product. In the culture analysis, the metabolic product generated by the organism attaches to the activated polymer by reaction with the intermediate coupling group.

Linking chemistry involving gluteraldehyde, cyanogen bromide, hydrazine, bisepoxirane, divinylsulfone, epichlorohydrin, periodate, trichlorotriazine, diazonium salts, carbonyldiimidazole, carbodimides, N-hydroxy succinimide, and tosylates has been described extensively in the art. A review of these chemistries and procedures is given in "Practical Guide for use in Affinity Chromatograph and Related Techniques", Reactifs IBF-Societe Chimique Pointet-Girard, Villeneuve-La-Garenne-France. Specific examples for the activation of pendent hydroxy groups by carbonyldiimidazol is reported in J. Biol Chem 254 (1979), 2572 and J Chromatogr. 219 (1981), pp. 353, 361. The activation of pendent carboxylic acid groups by water soluble carbodiimide is described in Biochem J. 199 (1981), pp. 297, 419. Activation of carboxylic acids by N-hydroxysuccinimide is described in Biochemistry 111, (1972) p. 2291, and Biophys. Acta 670 (1981) 163.

Typical water-soluble polymers that may be activated by these procedures may include polyhydroxyethyl methacrylate and acrylate, methylvinylether copolymers, polyvinyl alcohols and copolymers, and the polyampholytes described above. Other water-soluble polymers may also be used.

Thus, the design of a specific metabolic product responsive polymer for purposes of this invention is guided by the metabolic product to which it will complex (i.e. $H^+$ or a specific antibody) and by the environmental requirements of the organism to be assayed.

GROWTH MEDIA

The basic growth medium for the system contains nutrient materials selected for fermentation by the specific type cells to be analyzed. A specific metabolic product responsive polymer of the type described above is then added to the medium. The resulting medium can be optionally supplemented with growth regulators such as antibotics, amino acids, vitamins, salts, or lipids. The growth regulators, used separately or in combination, may be used to make the medium either highly selective for a specific cell type or less selective for a broad spectrum cell response. The composition of the nutrient medium enables the invention to respond flexibly to a variety of analytical needs.

Components for growth media are commercially available from Difco, Detroit Mich. and BBL, Cockeysville, Md., among other sources. The medium used to detect the *E. coli* in the examples below was Difco purple supplemented with 1% wt/volume carbohydrates. (Difco Manual of Dehydrated Culture Media and Reagents for Microbiology, page 712-715, (1984), Difco Laboratories, Detroit, Mich.).

The medium used in the illustrative examples set forth below was made by dissolving 10 g of porteose No. 3, 1 g of beef extract, 5 g sodium chloride, and bromo cresol purple dye (20 mg) in liter of purified water. For detection of growth in the presence of carbohydrate, 1% mannitol was added to the growth medium. Mannose, arabinose, lactose, and inositol were substituted for the mannitol to study the influence of specific carbohydrates.

Alternative media, including synthetic media, are well known and may be used to support the growth of particular organisms under study for characterization and identification.

CONCENTRATION OF THE METABOLIC PRODUCT RESPONSIVE POLYMER

Follwoing sterilization by conventional methods, the media was aseptically mixed with 0.1% wt/volume of the synthetic metabolic product responsive polymer. Before testing, the pH of the nutrient medium was adjusted as needed to a value compatible with the physiological requirements of the cell culture and the solubility requirments of the polymer. Alternatively, depending on the nature of the polymer, the medium containing the metabolic product responsive polymer can be sterilized after these pH adjustments.

Metabolic product-responsive polymer concentrations ranging from 0.1–2.0% wt/volume yielded effective results at all values, although the invention is not limited to this range. The lower end (0.1%) of this range is considered more desirable for three reasons. First, lower concentrations conserve polymer. Second, deleterious physiological effects of the polymer on the active cell culture are avoided. Third, the lower concentration minimizes buffering capacity of the growth medium so as to optimize the response resulting from adsorption of the altered polymer onto the piezoelectric sensor. In principle, lower polymer concentrations will result in greater sensitivity as the buffering capacity is minimized, whereas higher polymer concentrations can afford a greater dynamic range.

CELL CONCENTRATION DETERMINATION

Cell concentration in a given experiment was estimated microscopically in a Petroff-Hauser counting chamber. Growth of the cell culture was first arrested by the addition of 0.1% sodium azide solution. In some cases, the cell densities in the Petroff-Hauser counting chamber were counted automatically using an Olympus Q2 image analyzer equipped with a Compaq 386/25 computer.

PIEZOELECTRIC BIOSENSOR DEVICE AND SYSTEM

Cell detection and identification, antibiotic response studies, and growth rate determinations can be made either with a single piezoelectric oscillator device under the conditions outlined above or with a piezoelectric oscillator device referenced against a second quartz crystal that compensates for instabilities associated with temperature.

Figure 5:
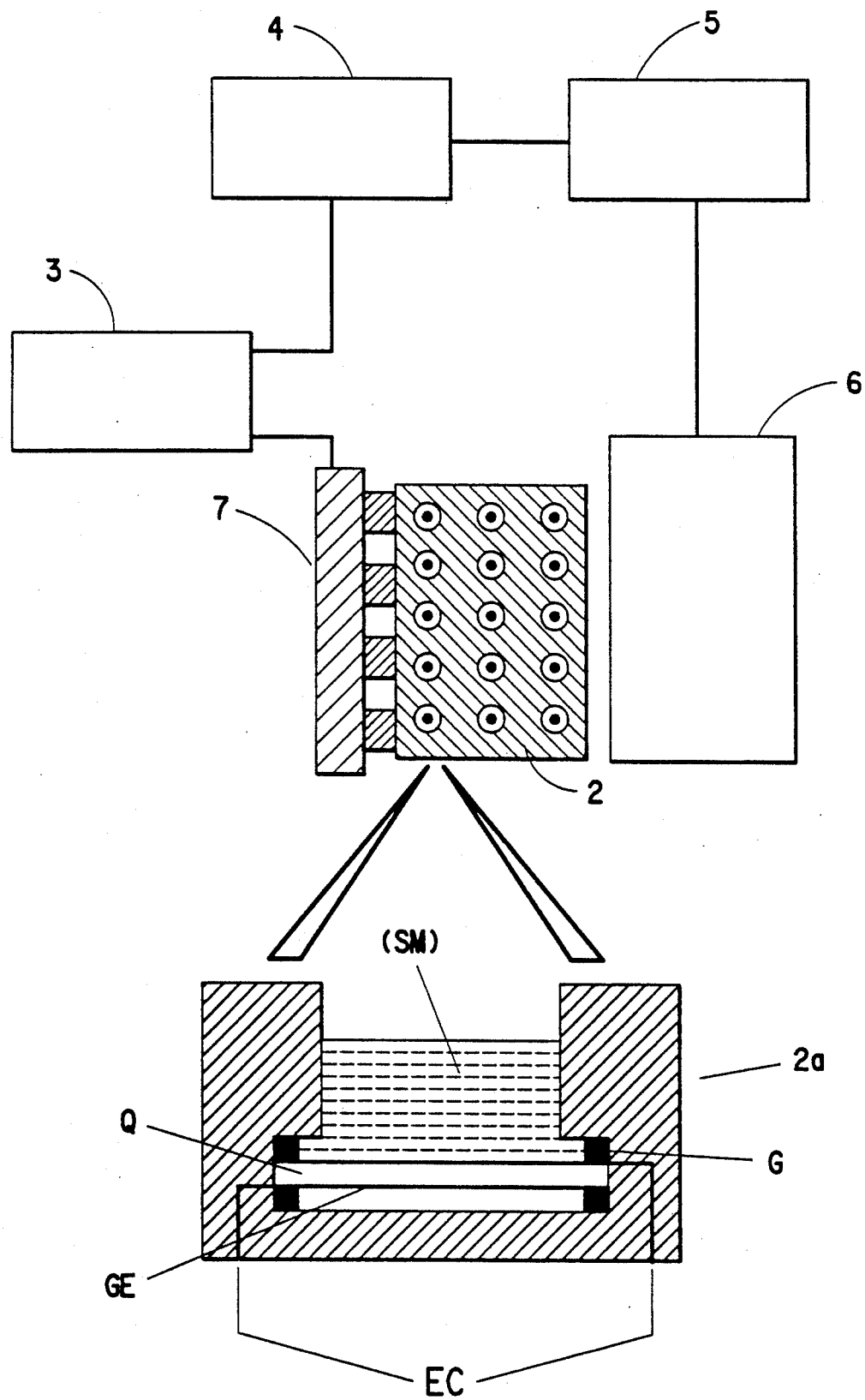
FIG. 5 is a schematic diagram of the elements of a system comprising oscillator circuits, frequency counters, a reagent delivery system, a multiple device plate for containing the culture, and a computer to analyze the resulting data. One device is shown in a blow-up view.

Additionally, a versatile mode of operation may be to perform assays in a multiwell analysis plate (2) associated with oscillator circuits (3), frequency counters (4), a reagent delivery system (6), a bus board connector (7), and a computer (5), the computer (5) capable of recording data and controlling a reagent delivery system. FIG. 5 shows a schematic of such a system including an enlargement of one device or reaction chamber (2a) of the multi-well anyalsis plate (2) containing a piezoelectric oscillator (Q, GE, and EC collectively), the sample medium (SM), and o-rings or gaskets (G) to a gold electrode (GE) on opposing faces of a quartz crystal (Q), the quartz crystal and electrodes supported by a gasket (G). Each piezoelectric sensor (2a) of the multiwell sensor array of the analysis plate (2) may be individually linked to the computer (5). Or each may be referenced against its own reference sensor or all sensors of the array may be referenced collectively to a common sensor. The reagent delivery system (6) would incorporate the necessary plumbing and controllers (i.e., pumps, servo moters, etc.) so that culture samples can be introduced into the multiple wells automatically. The reagent delivery system (6) also would be capable of adding either different nutrient media or different antibiotics as called for. The response pattern of the multiple sample wells would be correlated with the known reagent additions by computer analysis for cell identification or antibiotic response. Expert systems can be employed wherein response pattern recognition from known cultures in different media are "learned" by the computer, and then utilized for analysis.

To facilitate the discrete placement of specific reagents in the wells, the growth media can be prepared prior to analysis as a dried mixture, contained on or within a porous matrix such as a membrane or absorbent material such as described in U.S. Pat. No. 4,588,555. During testing the porous element would be positioned above each well. Sample fluid containing the cells could be added on top of the element or alternatively added to the well before positioning the reagent element.

An alternative device format immobilizes the organism on a membrane or porous structure that is then placed opposite, and in close proximity to, the surface of the piezoelectric oscillator. The production of metabolic products is followed by diffusion of those products into the reaction chamber defined by the quartz crystal, the membrane, and confining o-rings. After reaction with the receptor groups on the polymer in solution, the polymer precipitates and adsorbs onto the QCM surface, resulting in a measurable frequency change.

It is expected that the method will be especially valuable in detecting and identifying pathogenic bacteria and fungi. It may also be useful for detecting mammalian cells in culture by directly determining the presence of a unique metabolic product by means of a polymer or polymer conjugate specific to each different organism. Additionally, the method can use a polymer responsive to a metabolic product such as a proton that is commonly produced by all organisms, and thus can detect and identify the organism on the basis of its ability to metabolize a specific nutrient. Another significant use of the method is to determine rapidly the response of the organism to growth inhibitors. The sensitivity of bacteria and fungi to static or cidal chemicals and antibiotics and the response of cancer cells to chemotherapeutic agents are also good examples of the invention's usefulness. The versatility of the invention suggests many applications in clinical settings, microbial detection in foods, and quality control in industrial processes.

EXAMPLES

The following nonlimiting examples illustrate the basic principles and unique advantages of the present invention.

EXAMPLE 1.

QCM Frequency Response due to Chemically and Electrochemically Induced pH Changes.

This example illustrates the fact that changes in the pH of a medium can be detected by a QCM. Acid equivalents convert an anionic polymer to its isoelectric composition, thereby resulting in adsorption of the polymer on the surface of the quartz crystal of the QCM. The polymer adsorption results in a decrease in the resonant frequency of the QCM as measured from the time of introduction of the acid equivalents. The acid equivalent can be introduced by direct addition of acid or by water electrolysis at the gold electrode of the QCM. In either case, the pH at the QCM surface is altered.

(a) When a 1% aqueous solution of 1:1:1 AA-MMA-DMAEMA is acidified with 0.001N HCl to its isoelectric point from pH=7.5 in the QCM cell, a pronounced decrease in frequency is immediately observed (FIG. 6a). This is attributed primarily to an increase in mass on the quartz crystal due to adsorption of the polymer as the viscosity of the medium does not change appreciably. Polymer deposition is obvious in photographs of the quartz/gold surface which indicate thick adherent polymer films on the QCM surface. Further addition of acid or back-titration with 0.001N KOH returns the resonant frequency to the original frequency.

Figure 6B:
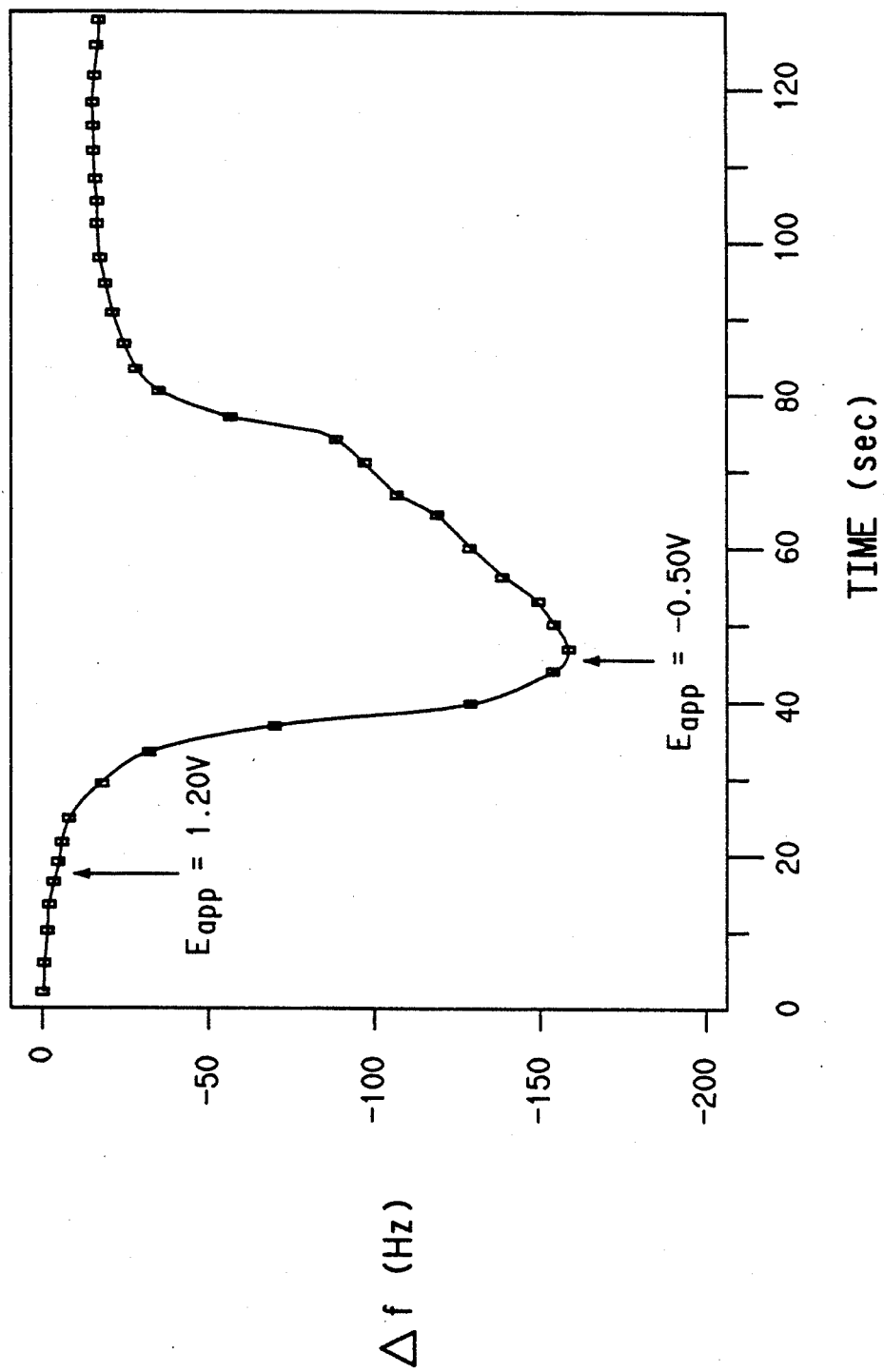
FIG. 6b is a graph showing changes in the resonant frequency of a OCM during chemical manipulation towards the isoelectric point of the metabolic product responsive polymer contained in a solution.

(b) Dependence of the polymer adsorption on pH can also be demonstrated by electrochemical manipulation of the pH. When the potential at the gold surface, in the presence of 1:1:1 AA-MMA-DMAEMA, was stepped to 1.2 V (vs Ag/AgCl) where $O_2$ is evolved, the pH at the electrode interface was lowered due to the formation of $H^+$ ions (eq 2). This resulted in the highly efficient deposition of the isoelectric polymer as it was generated at the interface, with concomitant decrease in frequency (FIG. 6b). Upon stepping the potential back to $-0.5$ V, the pH at the surface was increased due to the generation of $OH^-$ ions, and the frequency returns to near its original value (eq 3).

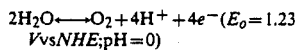
$$2H_2O \longleftrightarrow O_2 + 4H^+ + 4e^- (E_o = 1.23$$
$$V vs NHE; pH=0) \quad \text{(eq 2)}$$

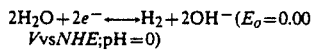
$$2H_2O + 2e^- \longleftrightarrow H_2 + 2OH^- (E_o = 0.00$$
$$V vs NHE; pH=0) \quad \text{(eq 3)}$$

EXAMPLE 2.

QCM Frequency Response due to the Presence of Active Cells and their Growth.

This example illustrates the use of a QCM to detect the presence of E. coli. Acid metabolic products converted an amphoteric polymer to its isoelectric composition, resulting in adsoption of the polymer on the surface of the QCM. The polymer adsorption results in a decrease in the resonant frequency of the QCM as measured from the time of E. coli introduction to the nutrient medium.

The invention has been demonstrated by the growth of E. coli bacteria in a nutrient medium, containing purple broth (Bacto), carbohydrate, beef extract and the 1:1:1 AA-MMA-DMAEMA terpolymer. A pH indicator dye was also added as an aid in corroborating behavior observed with the QCM. The methodology is as follows. A glass cell containing 0.75 mL of 1% mannitol, 0.1% beef extract (Bacto), 0.5% NaCl, 1.0% peptone (No. 3, Proteose), and 0.1% of 1:1:1 AA-MMA-DMAEMA terpolymer was inoculated with a small volume of an E. coli suspension so that the concentration was $10^8$ cells/mL. The solution was adjusted to pH=7.5 so as to ensure solubilization of the polymer and consistency of the growth medium. While monitoring the frequency, 75 uL of a sample containing $5.4 \times 10^{10}$ E. coli cells/mL were added so that the actual starting concentration of cells was $5.4 \times 10^8$ cells/mL. A layer of oil was then added to the top of this solution so as to exclude air from the medium. In each case, the QCM chamber was maintained at $37° \pm 1°$ C. throughout the course of the experiment.

Under these conditions the bacteria metabolize nutrient with concomitant release of organic acids and carbon dioxide. The metabolic activity causes a decrease in pH and supplies protons to the polymer. When the isoelectric point of the polymer is achieved, the polymer accumulates on the gold electrode of the QCM. The resulting increase in mass gives a corresponding decrease in the resonant frequency which is readily measured electronically (FIG. 7). The shift is significant, ranging from 1500 to several thousand Hz within two hours, depending on the initial conditions.

EXAMPLE 3.

Determination of Response of Cell Growth to Growth Regulators.

This example illustrates that E. coli metabolism can be suppressed by purposely added antibiotic.

A gold-coated quartz crystal was immersed in 0.75 mL of a sterile aqueous solution comprising 1% mannitol, 0.1% beef extract (Bacto), 0.5% NaCl, 1.0% peptone (No. 3, Proteose), and 0.1% of 1:1:1 AA-MMA-DMAEMA terpolymer. The solution was adjusted to pH=7.5 so as to ensure solubilization of the polymer and consistency of the growth medium. While monitoring the frequency, 75 uL of a sample containing $5.4 \times 10^{10}$ E. coli cells/mL were added so that the actual starting concentration of cells was $5.4 \times 10^9$ cells/mL. This was followed by addition of 15 $\mu$L of an antibiotic Kanamycin solution (25 $\mu$g/mL) yielding an actual concentration of Kanamycin of 0.5 $\mu$g/mL. The medium was then covered with an oil film to exclude air. The experiment was also performed at a cell concentration of $5.4 \times 10^8$ cells/mL. In each case, the QCM chamber was maintained at 37°±1° C. throughout the course of the experiment.

As summarized in Table B, the QCM frequency decreased markedly under conditions conductive to cell growth; i.e., in the absence of antibiotic. In contrast, the resonant frequency did not decrease in the presence of Kanamycin, indicating lack of cell growth. This result is also shown in FIG. 7.

TABLE B

Response of QCM to *E. coli* in the presence of Kanamycin.

| Starting bacteria concentration (cells/mL) | Kanamycin addition | QCM frequency change ($\Delta f$) after 10 min (Hz) |
| --- | --- | --- |
| $5.4 \times 10^9$ | No | −1500 |
| $5.4 \times 10^8$ | No | −600 |
| $5.4 \times 10^9$ | Yes | 0 |
| $5.4 \times 10^9$ | Yes | 0 |

EXAMPLE 4.

QCM Frequency Response due to the Presence of Bacterial Growth-Modulation of Response due to Different *E. coli* Concentrations.

This example illustrates that the QCM response is dependent upon the starting concentration of *E. coli* in the inoculum.

Figure 8:
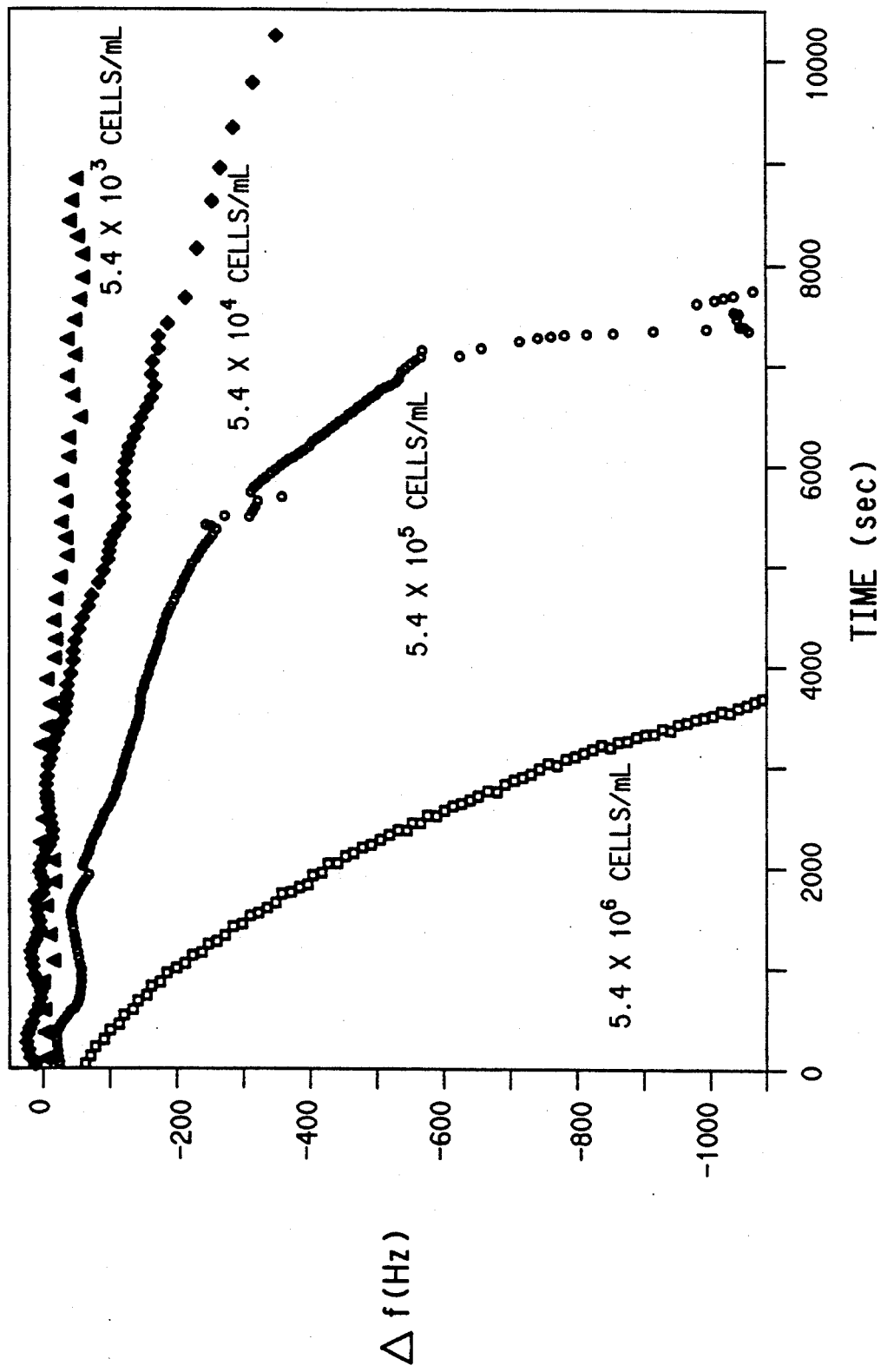
FIG. 8 is a graph showing a comparison of piezoelectric oscillator response over time from different starting concentrations of E. coli.

A gold-coated quartz crystal was immersed in 2 ml of a sterile aqueous solution comprising 1% mannitol, 0.1% beef extract (Bacto), 0.5% NaCl, 1.0% peptone (Proteose), and 0.1% of 1:1:1 AA-MMA-DMAEMA terpolymer. The solution was adjusted to pH=7.5 to ensure solubilization of the polymer. While monitoring the resonant frequency, 20 uL of a sample containing $5.4 \times 10^8$ *E. coli* cells/mL were added so that the starting concentration of cells in the medium was $5.4 \times 10^6$ cells/mL. The medium was then covered with an oil film to exclude air. The chamber was maintained at 37° C. throughout the experiment. During the course of incubation following addition of the oil film, acid was released from metabolic products of the bacteria rendering the polymer isoelectric and insoluble and the resonant frequency decreased due to deposition of polymer on the QCM surface. The rate of resonant frequency decrease, $d\Delta f/\Delta t$, became larger with time due to the increase in population of *E. coli* and concomitant increase in the generation of acid equivalents (FIG. 2). The response was dependent upon the amount of *E. coli* added to the well, decreasing for smaller concentrations. Table C depicts the relative rates in terms of the frequency shift after two hours. FIG. 8 shows a graphical comparison of the data acquired during cell growth.

TABLE C

Response of QCM to different concentrations of *E. coli*.

| Bacteria Concentration (cells/mL) | Frequency change ($\Delta f$) after 2 hr. (Hz) |
| --- | --- |
| $5.4 \times 10^6$ | $\geq -2000$ |
| $5.4 \times 10^5$ | −950 |
| $5.4 \times 10^4$ | −225 |
| $5.4 \times 10^3$ | −50 |

EXAMPLE 5.

Response of *E. coli* to Different Carbohydrate Nutrients.

This example illustrates the fact that the metabolic product formation and growth of *E. coli* is dependent upon the type of carbohydrate nutrient present in the incubation medium. The QCM response can be used to characterize the nutrient requirements of the organism, and suggests that cells of unknown identity can be identified by a nutrient response "fingerprint".

A gold-coated quartz crystal was immersed in 2 mL of a sterile aqueous solution comprising 1% carbohydrate, 0.1% beef extract (Bacto), 0.5% NaCl, 1.0% peptone (No. 3, Proteose), and 0.1% of 1:1:1 AA-MMA-DMAEMA terpolymer. The solution was adjusted to pH=7.5 to ensure solubilization of the polymer. While monitoring the resonant frequency, 20 uL of a sample containing $7.4 \times 10^7$ *E. coli* cells/mL were added so that the final concentration of cells was $7.4 \times 10^5$ cells/mL. The medium was then covered with oil to exclude air. As a control, QCM response was also determined for cell growth in the same media without added carbohydrate.

Figure 9:
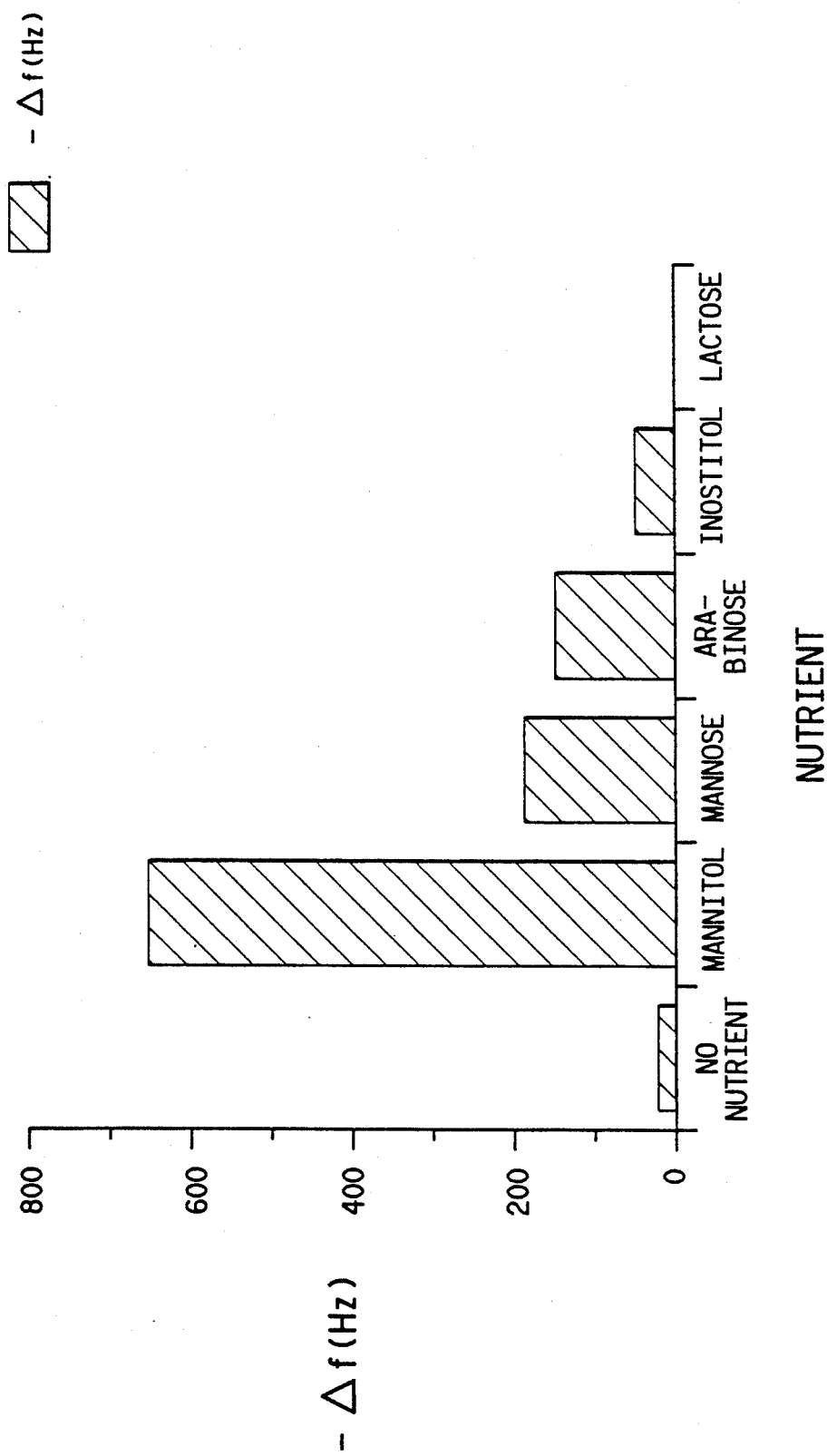
FIG. 9 is a bar graph showing the piezoelectric oscillator response of E. coli to different carbohydrate nutrients.

A positive QCM response (a frequency decrease) was observed for cell growth in the presence of mannitol, mannose and arabinose. Mannitol gave the most active response. Negligible or no frequency change was observed in the presence of lactose or inositol, or for experiments performed in the absence of carbohydrate nutrient (FIG. 9 and Table D).

TABLLE D

Response of QCM to *E. coli* in the presence of different carbohydrates*

| Carbohydrate | QCM frequency change ($\Delta f$) after 1 hr. (Hz) |
| --- | --- |
| 1% mannitol | −650 |
| 1% mannose | −180 |
| 1% arabinose | −140 |
| 1% inositol | −40 |
| 1% lactose | 0 |
| no carbohydrate | −20 |

*starting *E. coli* concentration = $7.4 \times 10^5$ cells/mL

EXAMPLE 6.

Indirect Determination of Cell Doubling Rates.

This example illustrates the point that Applicant's invention can determine the rate of cell growth, in terms of the time required for doubling the cell concentration.

Figure 10:
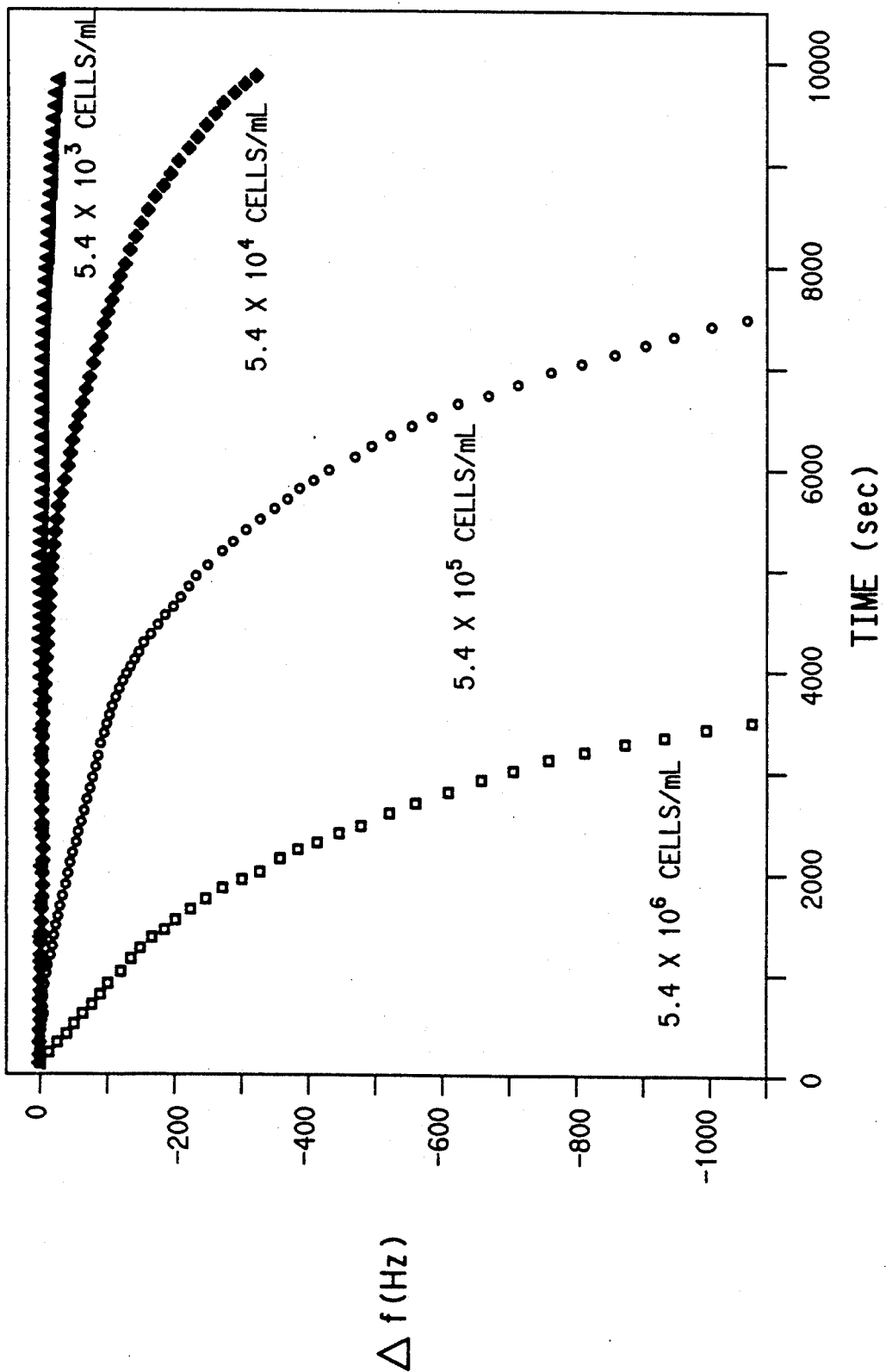
FIG. 10 is a graph showing the predicted behavior of resonant frequency changes over time for different cell concentrations using reported values of E. coli cell doubling and metabolic rate constant k.
Figure 11:
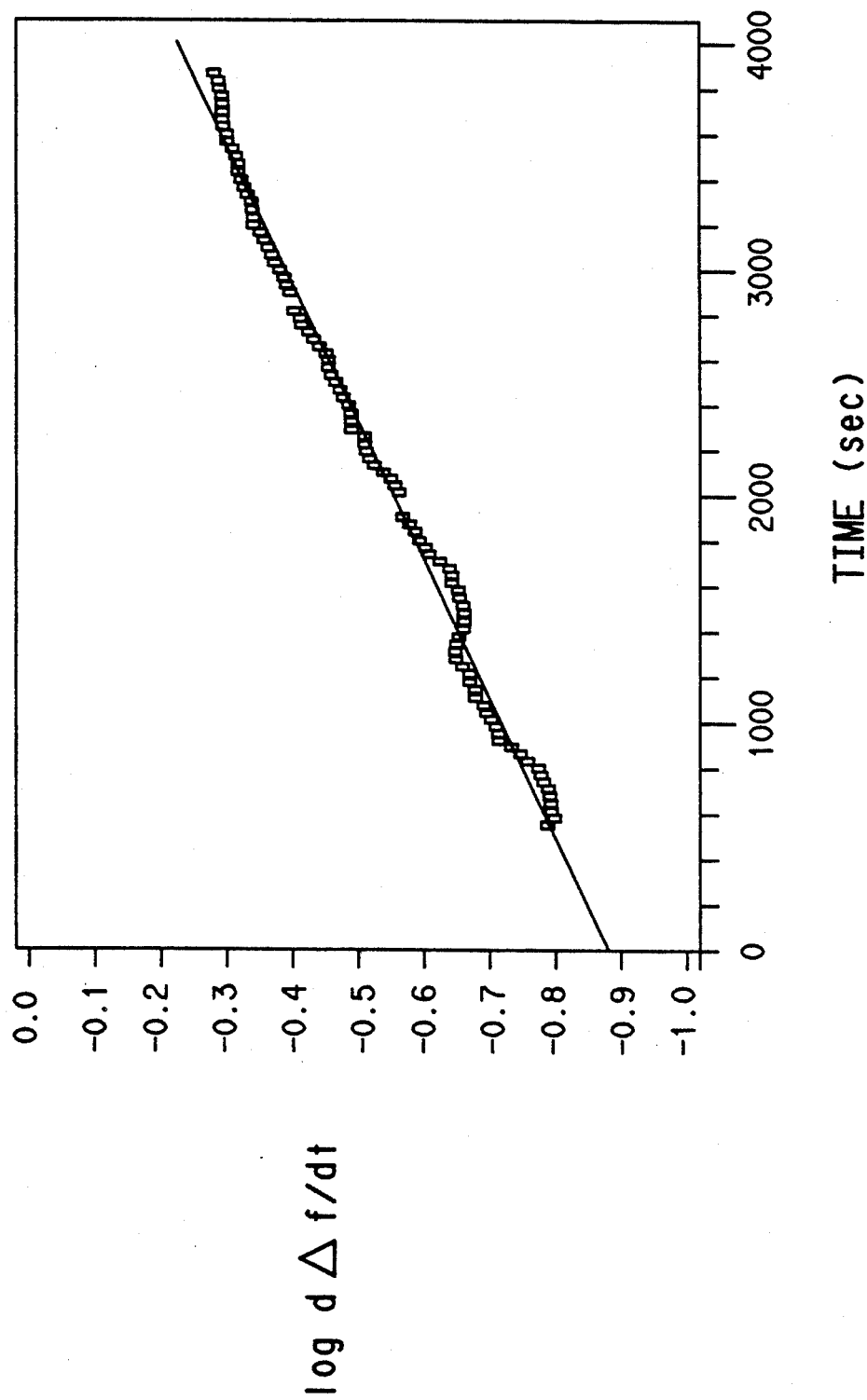
FIG. 11 is a graph showing the time interval for colony doubling as determined from a plot of log $\Delta f/\Delta t$.

In the presence of active cell growth, the rate of resonant frequency change, $d\Delta f/dt$, increases due to the increasing concentration of cells with time. The growth response can be modelled using the equations below. The geometric factor $2^{t/v}$ accounts for the cell multiplication, where t is the elapsed time and v is the time required for the cell colony to double its concentration. Using these equations, the predicted behavior of $d\Delta f/dt$ is illustrated in FIG. 10 for different cell concentrations using the reported values of *E. coli* cell doubling and metabolic rate constant k (Gerhard Gottschalk in "Bacterial Metabolism," pp. 236–243, 1985, Verlag-Springer, N.Y. and Frederick C. Neidhardt, Ed., "Escherichia Coli and Salmonella Typhimurium," Vol. 2, pp. 1578–1582 and 1537–1540 (1987), American Society for Microbiology, Washington, D.C.) The actual predicted changes in [H+] are converted to $\Delta f$ values by a multiplication factor denoted as "C" below. Good agreement is realized by comparison of this model to the actual data of Example 4. Using the data from the cell concentration of $5.4 \times 10^6$ cells/mL, the time interval for colony doubling can be determined from a plot of log dΔf/dt vs. t, which gives a slope of (log 2)/v (FIG. 11). The value of v determined from the slope of FIG. 11 is 1900 sec., nearly identical to the reported value of 1800 sec. Significantly, when cell growth is not operative, dΔf/dt=0. Therefore, the data from the QCM can be used to differentiate between cases wherein only metabolic products are produced and those in which metabolic production is accompanied by cell growth.

$$\text{rate} = \frac{d[H^+]}{dt} = k[B_0]\, 2^{t/v}$$

$$\frac{d[H^+]}{dt} \alpha \frac{d\Delta f}{dt} = k[B_0]\, 2^{t/v}$$

$$\log \frac{d\Delta f}{dt} = \log \frac{k[B_0]}{C} + \frac{t}{v} \log 2$$

The detailed description and specific examples provided above, while indicating preferred embodiments of the invention, are given by way of illustration only. Those skilled in the art, having the benefit of the teachings of the present invention as hereinabove set forth, can effect numerous changes and modifications thereof to adapt it to various uses and conditions. These modifications are to be construed as being encompassed within the scope of the present invention, as set forth in the appended claims.

We claim:

1. A method for detecting the presence of an organism or its growth by means of a piezoelectric oscillator, comprising:
    measuring the resonant frequency of a piezoelectric oscillator having a receptor unmodified by a receptor by contacting the piezoelectric oscillator with a medium containing a metabolic product responsive polymer;
    introducing into the medium an organism capable of producing a metabolic product;
    incubating the medium to permit the production of the such that the metabolic product reacts with the metabolic product-responsive polymer to yield a polymer-metabolic product complex which deposits on the piezoelectric oscillator;
    monitoring the medium for a change in the resonant frequency of the piezoelectric oscillator caused by the deposition of the polymer metabolic product complex onto the piezoelectric oscillator such that the change in resonant frequency of the piezoelectric oscillator is used to determine the concentration, the metabolism rate, or cell growth rate of the organism.

2. The method of claim 1, wherein the metabolic product responsive polymer is a water-soluble pH sensitive polymer.

3. The method of claim 2, wherein the metabolic product responsive polymer is a water-soluble amphoteric polymer with an isoelectric point in the physiological range.

4. The method of claim 3, wherein the metabolic product responsive polymer is an amphoteric copolymer comprising a first unit selected from the group consisting of acidic monomers, and a second unit selected from the group consisting of basic monomers.

5. The method of claim 4, wherein the acidic monomer is selected from the group consisting of acrylic acid, methacrylic acid, and monomers containing phosphoric acid and sulfinic acid groups.

6. The method of claim 4, wherein the basic monomer is selected from the group consisting of N,N-dimethylaminoethyl methacrylate, diethylaninoethyl methacrylate, t-butylaminoethyl methacrylate, morpholinoethyl methacrylate, piperidinoethyl methacrylate.

7. The method of claim 3, wherein the metabolic product responsive polymer is an amphoteric terpolymer comprising a first unit selected from the group consisting of acidic monomers, a second unit selected from the group consisting of basic monomers, and a third group selected from the group consisting of neutral monomers.

8. The method of claim 7, wherein the acidic monomer is selected from the group consisting of acrylic acid, methacrylic acid, and monomers containing phosphoric acid and sulfinic acid groups.

9. The method of claim 7, wherein the basic monomer is selected from the group consisting of N,N-dimethylaminoethyl methacrylate, diethylaninoethyl methacrylate, t-butylaminoethyl methacrylate, morpholinoethyl methacrylate, and piperidinoethyl methacrylate.

10. The method of claim 7, wherein the neutral monomer is selected from the group consisting of alkyl methacrylates, hydroxyethyl methacrylate hydroxypropyl methacrylate, vinyl pyrrolidone, hydrolyzed vinyl acetate, acrylamides, vinyl ethers, and styrene.

11. The method of claim 7, wherein the amphoteric metabolic product responsive polymer comprises a 1-1-1 molar ratio polymer of acrylic acid, methyl methacrylate, and N,N-dimethylaminoethyl methacrylate.

12. The method of claim 1, wherein the metabolic product responsive polymer incorporates a receptor selected from the group consisting of antibodies, antigens, polynucleic acids, lectins, tissue receptors, chelating agents, ligand binding proteins, and cell adhesion factors.

13. The method of claim 1, wherein the organism is selected from the group consisting of bacteria, fungi, and tissue cells.

14. The method of claim 1, wherein the medium further comprises a growth regulator specific for the organism selcted from the group consisting of antibiotics, amino acids, carbohydrates, vitamins, salts, and lipids.

15. The method of claim 14, wherein the growth regulator speciific for the organism is a carbohydrate selected from the group consisting of mannitol mannose, arabinose, inositol, and lactose.

* * * * *